(12) United States Patent
Shanahan et al.

(10) Patent No.: US 9,782,597 B2
(45) Date of Patent: Oct. 10, 2017

(54) ELECTRICAL STIMULATION SYSTEM WITH TOOL-LESS LEAD EXTENSION AND METHODS OF MAKING AND USING

(71) Applicant: Boston Scientific Neuromodulation Corporation, Valencia, CA (US)

(72) Inventors: Christopher Shanahan, Santa Rosa, CA (US); Geoffrey Abellana Villarta, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/960,640

(22) Filed: Dec. 7, 2015

(65) Prior Publication Data
US 2016/0158558 A1  Jun. 9, 2016

Related U.S. Application Data

(60) Provisional application No. 62/089,752, filed on Dec. 9, 2014.

(51) Int. Cl.
*A61N 1/00* (2006.01)
*A61N 1/375* (2006.01)
*A61N 1/05* (2006.01)

(52) U.S. Cl.
CPC ............. *A61N 1/3752* (2013.01); *A61N 1/05* (2013.01)

(58) Field of Classification Search
USPC .................................................. 607/2, 116
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |

(Continued)

OTHER PUBLICATIONS

International Search Report and Written Opinion for PCT Application No. PCT/US15/64190 mailed Feb. 22, 2016.

*Primary Examiner* — Nicole F Johnson
(74) *Attorney, Agent, or Firm* — Lowe Graham Jones PLLC; Bruce E. Black (57) ABSTRACT

A lead extension at least one lead extension body; terminals disposed along one end portion of the lead extension body(ies); a lead extension connector disposed along another end portion of the lead extension body(ies); and conductors electrically coupling the connector contacts in the lead extension connector to the terminals. The lead extension connector can include lead channels with non-straight paths to facilitate retention of leads. Alternatively, the lead extension connector can include one or more stretchable boots to each receive a lead when stretched and to grip the lead when relaxed. Alternatively, the lead extension connector can have two connector bodies with a pin channel and pin, respectively. When the pin is inserted into the pin channel, the pin compresses a portion of the connector body against the lead to retain the lead within the connector.

20 Claims, 9 Drawing Sheets

(56) References Cited

U.S. PATENT DOCUMENTS

| | | |
|---|---|---|
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2007/0150036 A1 | 6/2007 | Anderson |
| 2008/0208267 A1 | 8/2008 | Alexander et al. |
| 2010/0274115 A1 | 10/2010 | Werder et al. |
| 2011/0029052 A1 | 2/2011 | McDonald et al. |
| 2011/0093034 A1 | 4/2011 | Kast et al. |
| 2012/0053646 A1* | 3/2012 | Brase ............... A61N 1/3752 607/2 |
| 2012/0150202 A1 | 6/2012 | Chen et al. |
| 2012/0203302 A1 | 8/2012 | Moffitt et al. |
| 2014/0188201 A1 | 7/2014 | Pianca |
| 2014/0273602 A1 | 9/2014 | Bondhus et al. |
| 2014/0343646 A1 | 11/2014 | Leven |

\* cited by examiner

ELECTRICAL STIMULATION SYSTEM WITH TOOL-LESS LEAD EXTENSION AND METHODS OF MAKING AND USING

CROSS-REFERENCE TO RELATED APPLICATIONS

This application claims the benefit under 35 U.S.C. §119 (e) of U.S. Provisional Patent Application Ser. No. 62/089,752 filed Dec. 9, 2014, which is incorporated herein by reference.

FIELD

The present invention is directed to the area of implantable electrical stimulation systems and methods of making and using the systems. The present invention is also directed to implantable electrical stimulation systems having a lead extension that does not require a tool for coupling with the lead, as well as methods of making and using the lead extension and electrical stimulation system.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a lead extension for electrically coupling to at least one implantable electrical stimulation lead. The lead extension includes at least one lead extension body having a first end portion and an opposing second end portion; terminals disposed along the first end portion of the at least one lead extension body; a lead extension connector disposed along the second end portion of the lead extension body; and conductors extending along the at least one lead extension body and electrically coupling connector contacts in the lead extension connector to the terminals. The lead extension connector mechanically receives a proximal end portion of at least one electrical stimulation lead. The lead extension connector includes a connector body, at least one lead channel defined within the connector body to receive the at least one electrical stimulation lead, and connector contacts disposed within the connector body to make electrical contact with terminals disposed on the at least one electrical stimulation lead. The at least one lead channel forms a non-straight path within the connector body so that, when the at least one electrical stimulation lead is received within the at least one lead channel, the at least one lead channel defines points of compression that facilitate retention of the at least one electrical stimulation lead within the lead extension connector.

In at least some embodiments, the at least one lead channel is two lead channels with each lead channel configured and arranged to receive an electrical stimulation lead. In at least some embodiments, each of the at least one lead channel includes at least two curves. In at least some embodiments, the at least two curves include a first curve and a second curve in a direction opposite the first curve.

Another embodiment is a method of coupling an electrical stimulation lead to the lead extension described above. The method includes bending a portion of the connector body of the lead extension; advancing a proximal end portion of the electrical stimulation lead into a one of the at least one lead channel of the lead extension so that a plurality of terminals of the electrical stimulation lead make electrical contact with the connector contacts of the lead extension; and inserting a second portion of the electrical stimulation lead into a non-straight section of the lead channel. When the connector body is no longer bent, the non-straight section of the lead channel forms one or more points of compression against the second portion of the electrical stimulation lead to retain the electrical stimulation lead within the lead extension connector.

Yet another embodiment is a lead extension for electrically coupling to at least one implantable electrical stimulation lead. The lead extension includes at least one lead extension body having a first end portion and an opposing second end portion; terminals disposed along the first end portion of the at least one lead extension body; a lead extension connector disposed along the second end portion of the lead extension body; and conductors extending along the at least one lead extension body and electrically coupling connector contacts in the lead extension connector to the terminals. The lead extension connector mechanically receives a proximal end portion of at least one electrical stimulation lead. The lead extension connector includes a connector body, at least one boot coupled to the connector body with each of the at least one boot being stretchable between a relaxed position and a stretched position, at least one lead channel defined within the connector body with each of the at least one lead channel extending through a one of the at least one boot, and connector contacts disposed within the connector body and configured and arranged to make electrical contact with terminals disposed on the at least one electrical stimulation lead when the at least one electrical stimulation lead is received in the at least one lead channel. Each of the at least one lead channel is configured and arranged to receive the at least one electrical stimulation lead.

In at least some embodiments, the at least one boot is two boots and the at least one lead channel is two lead channels with each lead channel configured and arranged to receive an electrical stimulation lead. In at least some embodiments, each of the at least one boot comprises a series of ridges and valleys. In at least some embodiments, each boot permits loading an electrical stimulation lead into the lead extension connector when the boot is in the stretched position and gripping the electrical stimulation lead when the boot is in the relaxed position.

A further embodiment, is a method of coupling an electrical stimulation lead to the lead extension of described above. The method includes stretching a one of the at least one boot of the lead extension connector into the stretched position; advancing a proximal end portion of the electrical stimulation lead into the lead channel so that a plurality of terminals of the electrical stimulation lead make electrical contact with the connector contacts of the lead extension; and returning the one of the at least one boot of the lead extension to the relaxed position. When the one of the least one boot of the lead extension is in the relaxed position, the one of the at least one boot forms a friction or compression fit with the electrical stimulation lead to retain the electrical stimulation lead within the lead extension connector.

Another embodiment is a lead extension for electrically coupling to at least one implantable electrical stimulation lead. The lead extension includes at least one lead extension body having a first end portion and an opposing second end portion; terminals disposed along the first end portion of the at least one lead extension body; a lead extension connector disposed along the second end portion of the lead extension body; and conductors extending along the at least one lead extension body and electrically coupling connector contacts in the lead extension connector to the terminals. The lead extension connector mechanically receives a proximal end portion of at least one electrical stimulation lead. The lead extension connector includes a first connector body defining a pin channel, a second connector body having a pin where a dimension of the pin is greater than a corresponding dimension of the pin channel, at least one lead channel defined within the first and second connector bodies to receive the at least one electrical stimulation lead, and connector contacts disposed within the first connector body to make electrical contact with terminals disposed on the at least one electrical stimulation lead when the at least one electrical stimulation lead is received in the at least one lead channel. The pin channel is configured and arranged to receive the pin and, when the pin is received in the pin channel, compress a portion of the first connector body against the at least one electrical stimulation lead in the at least one lead channel to facilitate retention of the at least one electrical stimulation lead within the at least one lead channel.

In at least some embodiments, the at least one lead channel is two lead channels and each lead channel is configured and arranged to receive an electrical stimulation lead. In at least some embodiments, the pin has a first pin portion and a second pin portion attached to the first pin portion and having sloping sides; the pin channel has a first channel portion and a second channel portion adjacent the first channel portion; where a dimension of the second pin portion is greater than a corresponding dimension of the second channel portion.

Another embodiment is a method of coupling an electrical stimulation lead to the lead extension described above. The method includes inserting the electrical stimulation lead in the lead channel defined through both the first and second connector bodies with the first and second connector bodies separated; and advancing the pin of the second connector body into the pin channel of the first connector body causing the portion of the first connector body to compress against the at least one electrical stimulation lead in the at least one lead channel to facilitate retention of the at least one electrical stimulation lead within the at least one lead channel.

Yet another embodiment is an electrical stimulation system that includes any of the lead extensions described above and at least one electrical stimulation lead. In at least some embodiments, the electrical stimulation system also includes a control module configured and arranged to receive the first end portion of the lead extension and electrically couple to the terminals of the lead extension.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed implantable electrical stimulation systems having a lead extension that does not require a tool for coupling with the lead, as well as methods of making and using the lead extension and electrical stimulation system.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
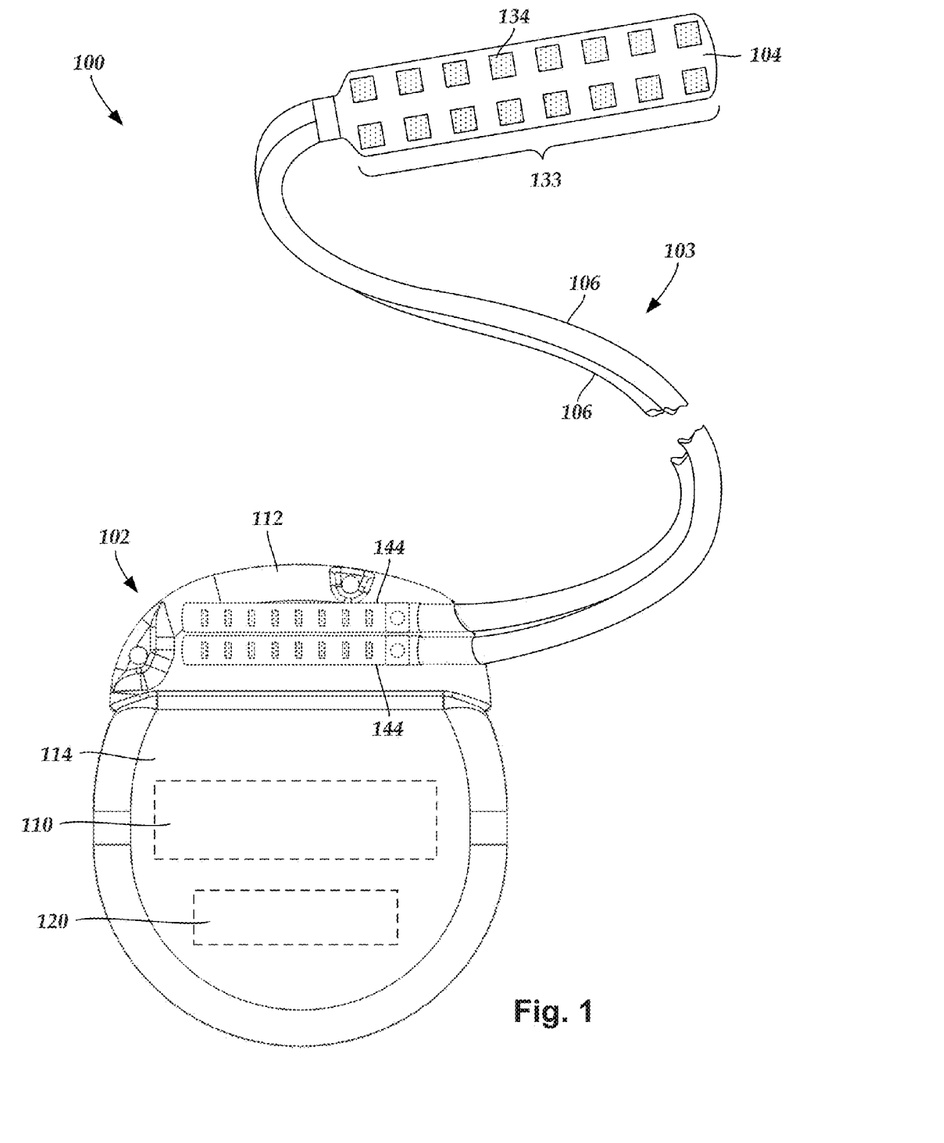
FIG. 1 is a schematic side view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
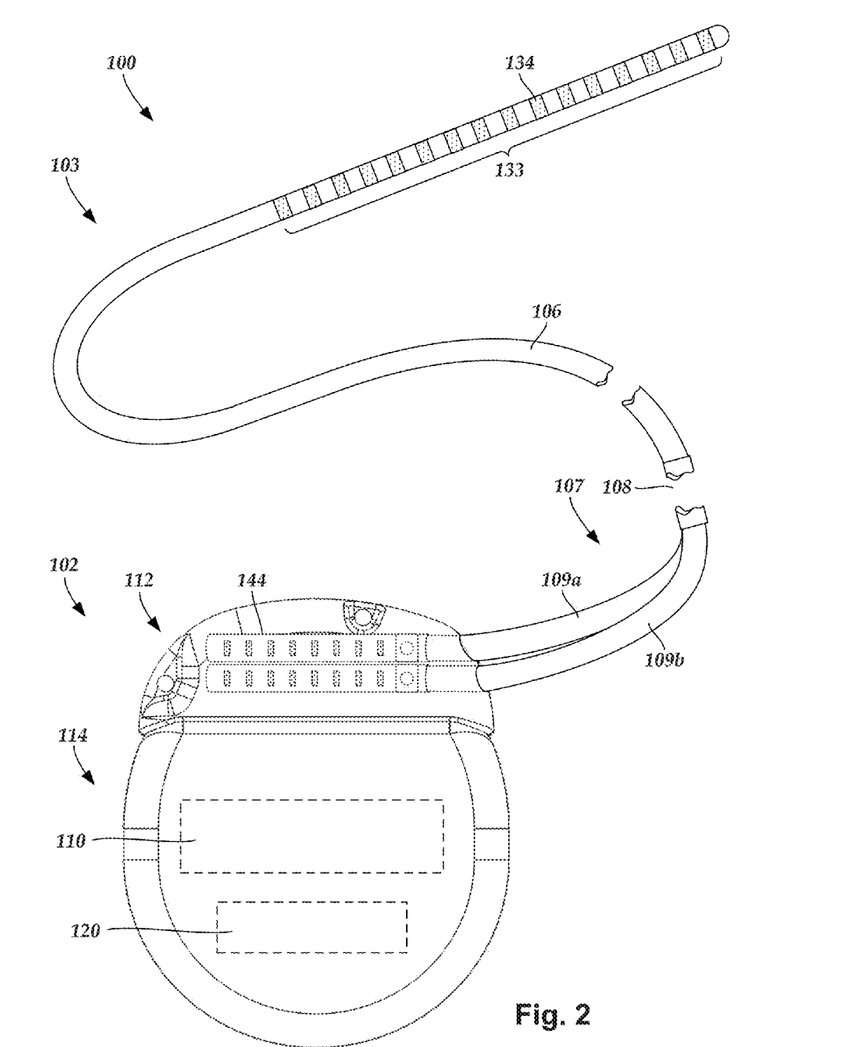
FIG. 2 is a schematic side view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
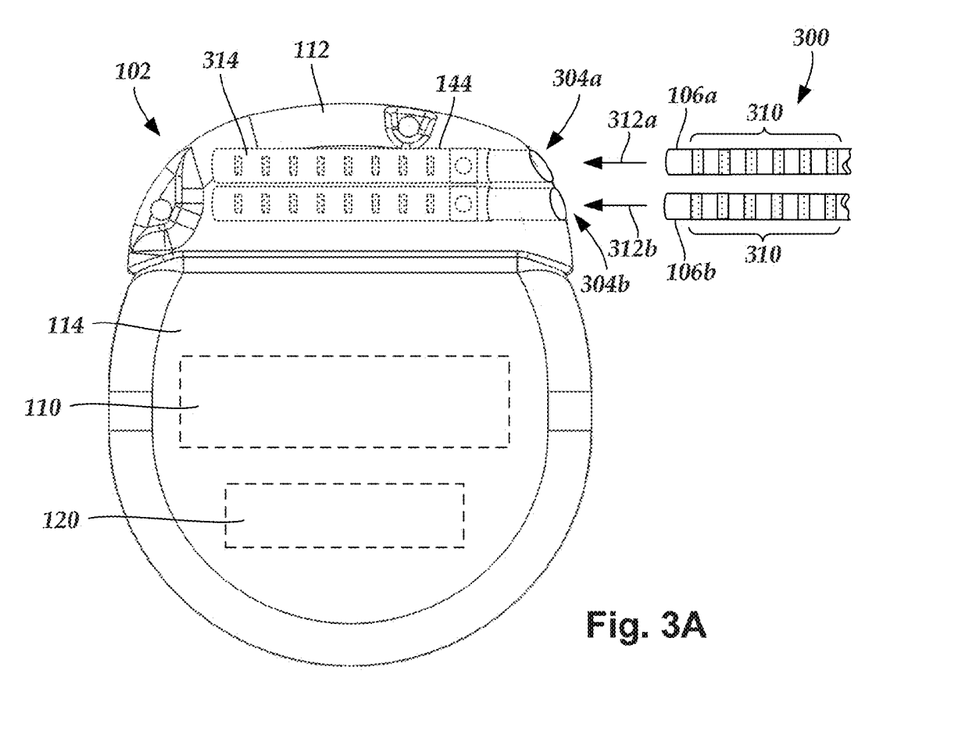
FIG. 3A is a schematic side view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312*a* and 312*b*. In FIG. 3A (and in other figures), the connector housing 112 is shown having two ports 304*a* and 304*b*. The connector housing 112 can define any suitable number of ports including, for example, one, two, three, four, five, six, seven, eight, or more ports.

The control module connector 144 also includes a plurality of connector contacts, such as connector contact 314, disposed within each port 304*a* and 304*b*. When the elongated device 300 is inserted into the ports 304*a* and 304*b*, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
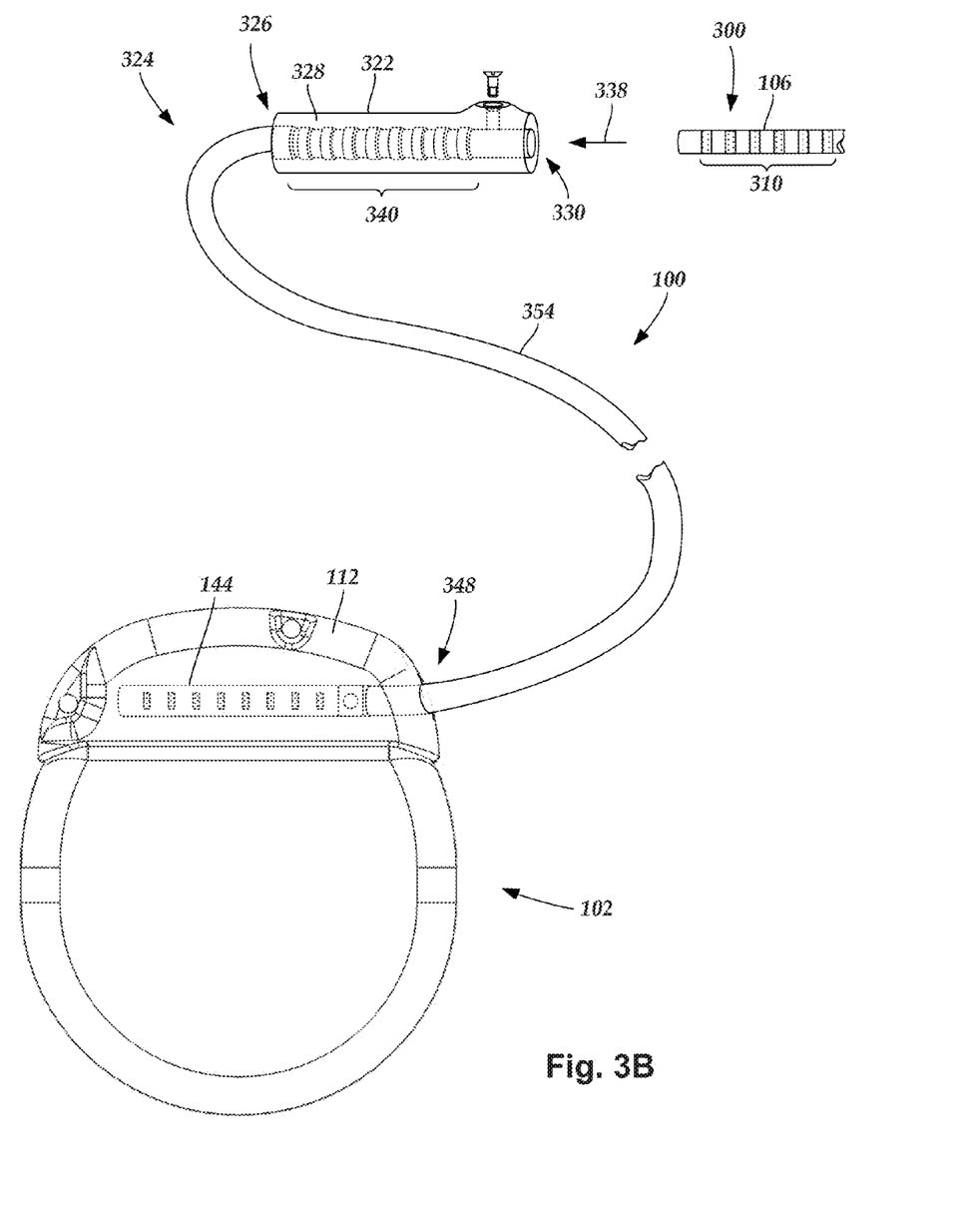
FIG. 3B is a schematic side view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324 and an extension body 354 extends from the connector to terminals (not shown) that can be inserted into the control module 102. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that extend along the extension body 354 and electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Conventionally, a set screw or other attachment element is used to fasten the lead within the connector of the lead extension. The set screw and other attachment elements often require the use of a tool, such as a torque wrench, to secure the lead into the extension. The use of a tool requires an extra component (i.e., the tool) during surgery and may also require additional surgical time. It may be desirable to utilize a connector that reliably fastens the lead within the connector of the lead extension without using a tool.

In addition, many conventional lead extensions are arranged to couple to only a single lead. It may be desirable to have a lead extension with a connector that can couple to two or more leads simultaneously. A number of different lead extension connectors are described below. Design considerations and the description of an element of one embodiment are also applicable to similarly names elements of the other embodiments unless indicated otherwise.

Figure 4A:
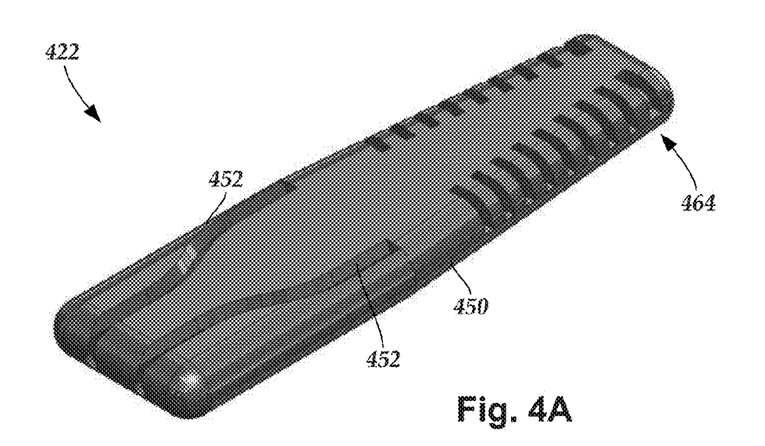
FIG. 4A is a schematic perspective view of one embodiment of a lead extension connector, according to the invention.
Figure 4B:
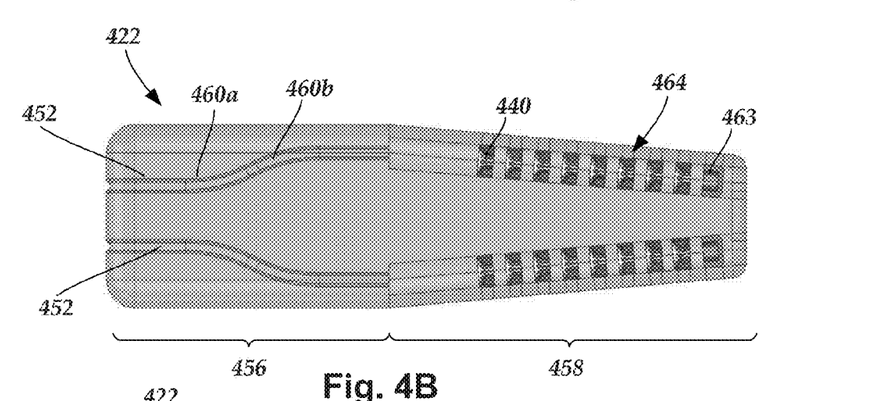
FIG. 4B is a schematic top perspective view of the lead extension connector of FIG. 4A, according to the invention.
Figure 4C:
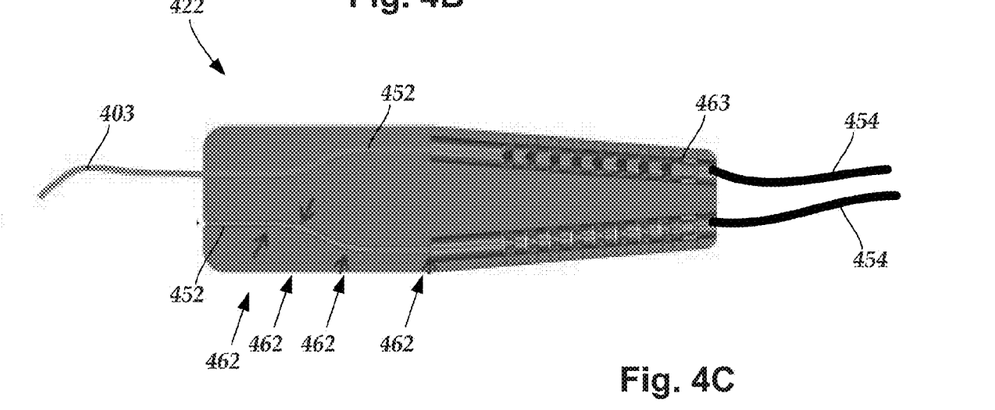
FIG. 4C is a schematic top perspective view of the lead extension connector of FIG. 4A with one lead inserted, according to the invention.

FIGS. 4A-4C illustrate one embodiment of a lead extension connector 422 that does not require a tool for coupling leads 403 (FIG. 4C) to the lead extension and which accommodates two leads. The lead extension connector 422 includes a connector body 450, one or more lead channels 452, and multiple connector contacts 440 (best seen in FIG. 4B). One or more lead extension bodies 454 (FIG. 4C) extend from the lead extension connector 422. The illustrated embodiment of FIG. 4C has two lead extension bodies 454, but it will be understood that a particular lead extension can have one, two, three, four, or more lead extension bodies 454 extending from the lead extension connector 422. In some embodiments, the number of lead extension bodies equals the number of leads that can be coupled to the lead extension connector. In other embodiments, the number of lead extension bodies is fewer or more than the number of leads that can be coupled to the lead extension connector. In at least some embodiments, the lead extension connector 422 may also include a lead end stop 463 (FIGS. 4B and 4C) which the proximal tip of the lead contacts when the lead 403 (FIG. 4C) is correctly inserted.

The illustrated lead extension connector 422 has two lead channels 452 and can accept the proximal ends of two leads (or the proximal ends of two lead bodies of the same lead—see, FIG. 2). It will be understood, however, that the lead extension connector can be formed with sufficient lead channels to receive the proximal end(s) of only one lead or of three, four, or more leads.

In at least some embodiments, the connector body 450 is made of a soft polymeric material, such as silicone, polyurethane, a rubber, or any combination thereof, for patient comfort. The connector body 450 optionally includes a more rigid section, which may be covered in the soft polymeric material, to securely hold the connector contacts 440 in place. In other embodiments, at least a lead loading section 456 (FIG. 4B) is made of a soft polymeric material so that it can be bent downward, relative to the remainder of the lead extension connector 422, so that the lead can be loaded in a lead connection section 458 (FIG. 4B). The lead connection section 458 may or may not be made, in whole or in part, with a soft polymeric material.

The connector contacts 440 are disposed in the lead connection section 458 and are arranged to make electrical contact with terminals on the lead when the lead is positioned correctly. The lead extension connector 422 optionally includes one or more windows 464 through which an observer can determine if the lead is inserted correctly. In the illustrated embodiment, if a lead terminal is observed within the window then the terminal may not be in contact with the connector contacts 440 which may indicate that the lead is inserted incorrectly. The windows 464 may be filled with transparent plastic.

To fasten the lead with the lead extension connector 422, the lead channel 452 has a non-straight path. In at least some embodiments, the lead channel 452 has a path with at least one curve 460*a*, 460*b* (FIG. 4B). In at least some embodiments, the lead channel 452 has a path with at least two curves 460*a*, 460*b* with the two curves optionally being in different directions (for example, clockwise and counterclockwise; left and right; or the like) relative to an end of the lead extension connector (for example, the end from which the lead extends). The lead channel 452 can have a tortuous path. A lead channel 452 with curves 460*a*, 460*b* has natural points 462 (FIG. 4C) of compression along the curves that hold the lead in place. In at least some embodiments, the lead channel 452 also has a diameter that is the same as, or slightly larger or smaller, than the diameter of the lead. If the lead channel 452 has the same or slightly smaller diameter of the lead, the lead channel may form a friction or compression fit with the portion of the lead disposed in the lead channel. It will be understood that the diameter of the lead channel may be uniform or non-uniform along the length of the lead channel. Optionally, the lead channel 452 may have a lip at the top of the channel to further assist in retaining the lead within the lead channel.

In at least some embodiments, to load the lead into the lead channel 452, the lead loading section 456, or a portion of the lead loading section to one side or the other of the lead channel 452, can be bent down and the proximal end portion of the lead can be inserted into the portion of the lead channel in the lead connection section 458 and the terminals on the lead can be aligned with the connector contacts 440. An adjacent portion of the lead can then be pushed or otherwise inserted into the portion of the lead channel 452 in the lead loading section 456. In other embodiments, the lead loading section 456 is not bent, but the proximal end of the lead is inserted into the lead connection section 458 and the lead is inserted (for example, pushed or otherwise loaded) simultaneously or subsequently into the lead channel 452 in the lead loading section 456.

Figure 5A:
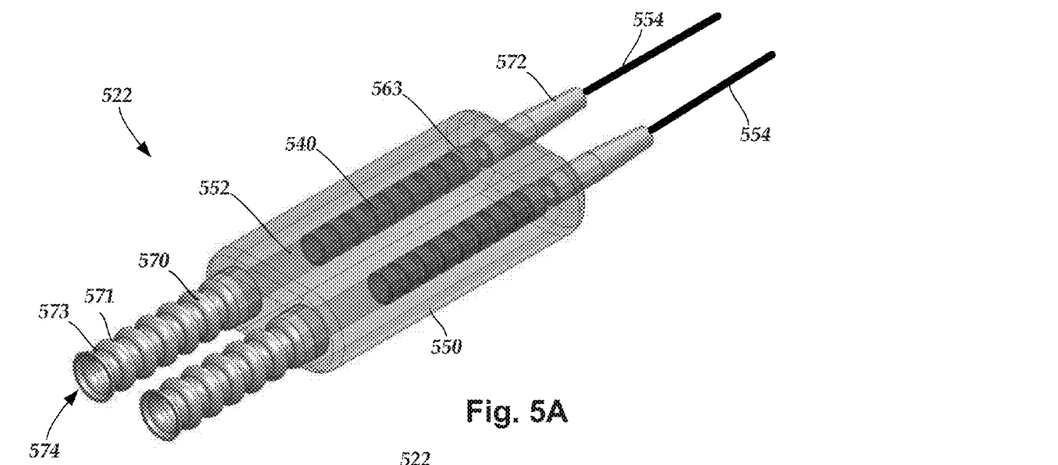
FIG. 5A is a schematic perspective view of a second embodiment of a lead extension connector, according to the invention.
Figure 5B:
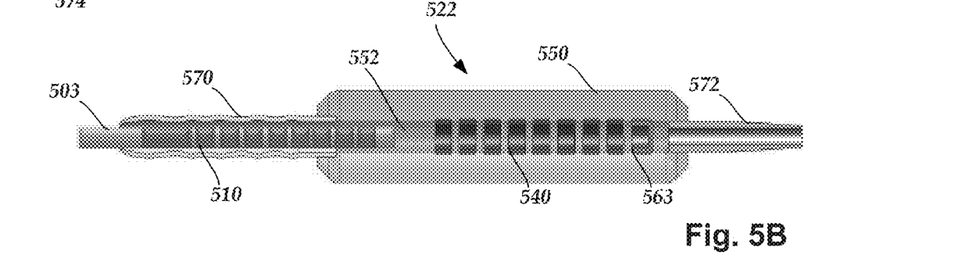
FIG. 5B is a schematic cross-sectional view of the lead extension connector of FIG. 5A with a boot in a stretched position and receiving a lead, according to the invention.
Figure 5C:
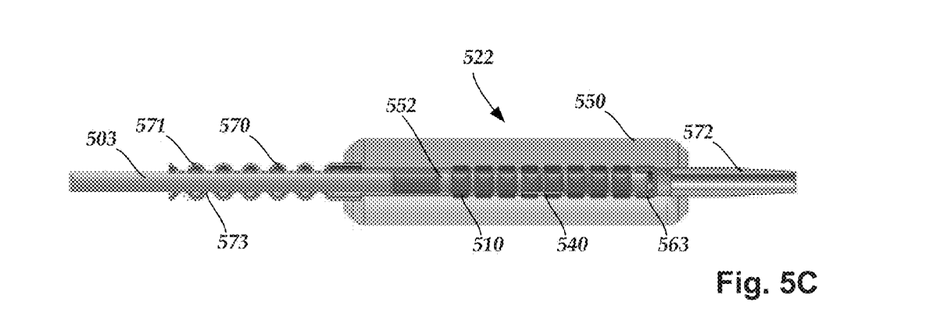
FIG. 5C is a schematic cross-sectional view of the lead extension connector of FIG. 5A with the boot in relaxed position and one lead inserted, according to the invention.

FIGS. 5A-5C illustrate another embodiment of a lead extension connector 522 that does not require a tool for coupling leads 503 (FIGS. 5B and 5C) to the lead extension and which accommodates two leads. The lead extension connector 522 includes a connector body 550, one or more lead channels 552, one or more boots 570, multiple connector contacts 540, and one or more optional strain relief sections 572. One or more lead extension bodies 554 (FIG. 5A) extend from the lead extension connector 522. The illustrated embodiment of FIG. 5A has two lead extension bodies 554, but it will be understood that a particular lead extension can have one, two, three, four, or more lead extension bodies 554 extending from the lead extension connector 522. In some embodiments, the number of lead extension bodies equals the number of leads that can be coupled to the lead extension connector. In other embodiments, the number of lead extension bodies is fewer or more than the number of leads that can be coupled to the lead extension connector. In at least some embodiments, the lead extension connector 522 may also include a lead end stop 563 which the proximal tip of the lead contacts when the lead is correctly inserted.

The illustrated lead extension connector 522 has two lead channels 552 and can accept the proximal ends of two leads (or the proximal ends of two lead bodies of the same lead—see, FIG. 2). It will be understood, however, that the lead extension connector can be formed with sufficient lead channels to receive the proximal end(s) of only one lead or of three, four, or more leads.

In at least some embodiments, the connector body 550 is made of a soft polymeric material, such as silicone, polyurethane, a rubber, or any combination thereof, for patient comfort. The connector body 550 optionally includes a more rigid section, which may be covered in the soft polymeric material, to securely hold the connector contacts 540 in place.

The connector contacts 540 are disposed in the lead body 550 and are arranged to make electrical contact with terminals 510 (FIGS. 5B and 5C) on the lead when the lead is positioned correctly, as illustrated in FIG. 5C. The lead extension connector 522 optionally includes one or more windows (not shown) through which an observer can determine if the lead is inserted correctly. In the illustrated embodiment, if a lead terminal is observed within the window then the terminal may not be in contact with the connector contacts 540 which may indicate that the lead is inserted incorrectly. The windows may be filled with transparent plastic.

To fasten the lead with the lead extension connector 522, each boot 570 has a tubular shape with an aperture 574 and is made of an elastic material. Each boot includes a series of ridges 571 and valleys 573 and the valleys define a minimum inner diameter for the boot. To load a lead 503, the boot 570 is stretched to depress the ridges 571 and elevate the valleys 573, as illustrated in FIG. 5B, which gives the boot 570 in the stretched state a larger minimum inner diameter than when the boot 570 is in the relaxed state (FIGS. 5A and 5C). The lead 503 can then be loaded into the lead extension connector 522, as illustrated in FIG. 5B, and the terminals 510 on the proximal end of the lead can make contact with the contact connectors 540. After loading the lead 503, the boot 570 can be released so that it returns to its relaxed state, as illustrated in FIG. 5C. The valleys 573 of the boot 570 produce regions with a smaller inner diameter that contacts and forms a friction or compression fit with portions of the lead 503 to hold the lead in place. The lead 503 can be released by pulling on the boot to stretch the boot, as illustrated in FIG. 5B, and then pulling the lead 503 out of the lead extension connector 522.

Figure 6A:
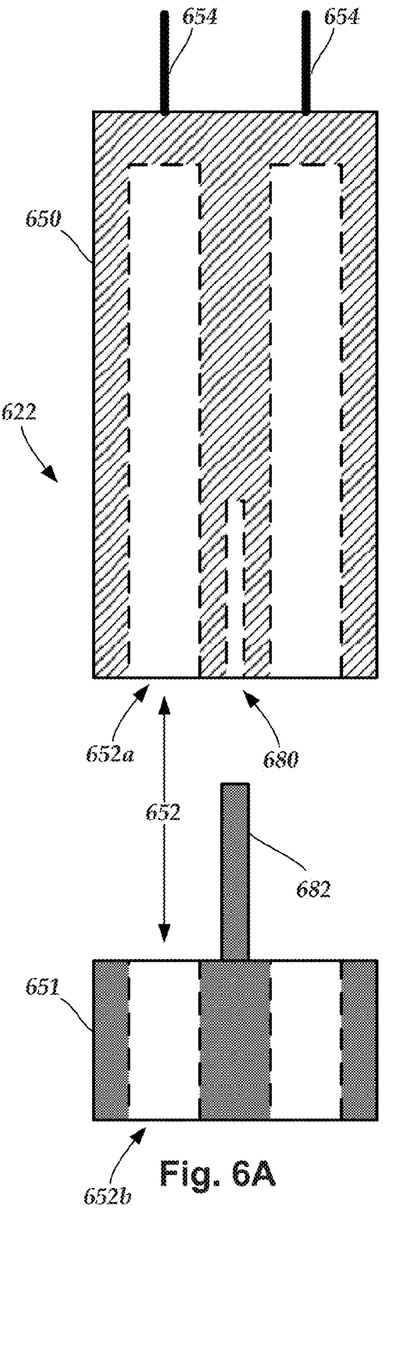
FIG. 6A is a schematic cross-sectional view of a third embodiment of a lead extension connector, according to the invention.
Figure 6B:
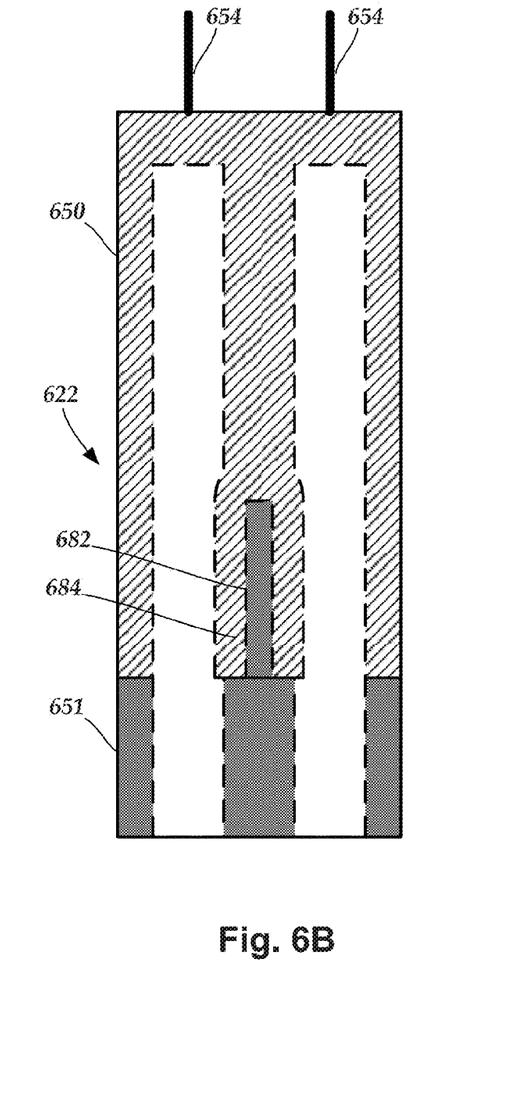
FIG. 6B is a schematic cross-sectional view of the lead extension connector of FIG. 6A with the pin of a second connector body inserted into a pin channel of a first connector body, according to the invention.

FIGS. 6A-6B illustrate another embodiment of a lead extension connector 622 that does not require a tool for coupling leads to the lead extension and which accommodates two leads. The lead extension connector 622 includes a first connector body 650, a second connector body 651, one or more lead channels 652, and multiple connector contacts (not shown). One or more lead extension bodies 654 extend from the lead extension connector 622. The illustrated embodiment has two lead extension bodies 654, but it will be understood that a particular lead extension can have one, two, three, four, or more lead extension bodies 654 extending from the lead extension connector 622. In some embodiments, the number of lead extension bodies equals the number of leads that can be coupled to the lead extension connector. In other embodiments, the number of lead extension bodies is fewer or more than the number of leads that can be coupled to the lead extension connector. In at least some embodiments, the lead extension connector 622 may also include a lead end stop (not shown) which the proximal tip of the lead contacts when the lead is correctly inserted.

The illustrated lead extension connector 622 has two lead channels 652 and can accept the proximal ends of two leads (or the proximal ends of two lead bodies of the same lead—see, FIG. 2). It will be understood, however, that the lead extension connector can be formed with sufficient lead channels to receive the proximal end(s) of only one lead or of three, four, or more leads.

In at least some embodiments, the connector body 650 is made of a soft polymeric material, such as silicone, polyurethane, a rubber, or any combination thereof, for patient comfort. The connector body 650 optionally includes a more rigid section, which may be covered in the soft polymeric material, to securely hold the connector contacts 640 in place.

The connector contacts are disposed in the lead body 650 and are arranged to make electrical contact with terminals on the lead when the lead is positioned correctly. The lead extension connector 622 optionally includes one or more windows (not shown) through which an observer can determine if the lead is inserted correctly. In the illustrated embodiment, if a lead terminal is observed within the window then the terminal may not be in contact with the connector contacts which may indicate that the lead is inserted incorrectly. The windows may be filled with transparent plastic.

The first connector body 650 has a first portion 652a of each lead channel 652 and further defines a pin channel 680. The second connector body has a second portion 652b of each lead channel and a pin 682. The pin 682 has a lateral width or diameter that is greater than the lateral width or diameter of the pin channel 680. When the pin 682 is inserted into the pin channel 680, portions 684 of the first connector body 650 adjacent the pin channel 680 are compressed and, consequently, compress adjacent portions of the lead channel 562, as illustrated in FIG. 6B.

To fasten the lead with the lead extension connector 622, each lead is inserted through both portions 562a, 562b of a lead channel 562 with the first connector body 650 and second connector body 651 separated. The terminals on the lead are aligned with the connector contacts in the first connector body 650. The pin 682 of the second connector body 651 is then inserted into the pin channel 680 of the first connector body 650. This insertion causes portions 684 of the first connector body 650 adjacent the pin channel 680 to be compressed and, consequently, compress adjacent portions of the lead channel 652, as illustrated in FIG. 6B, which then forms a frictional or compression fit against the lead. To release the lead, the second connector body 651 can be pulled back so that the pin 682 exits the pin channel 680 to release the compression and allows the lead to be removed.

Figure 7A:
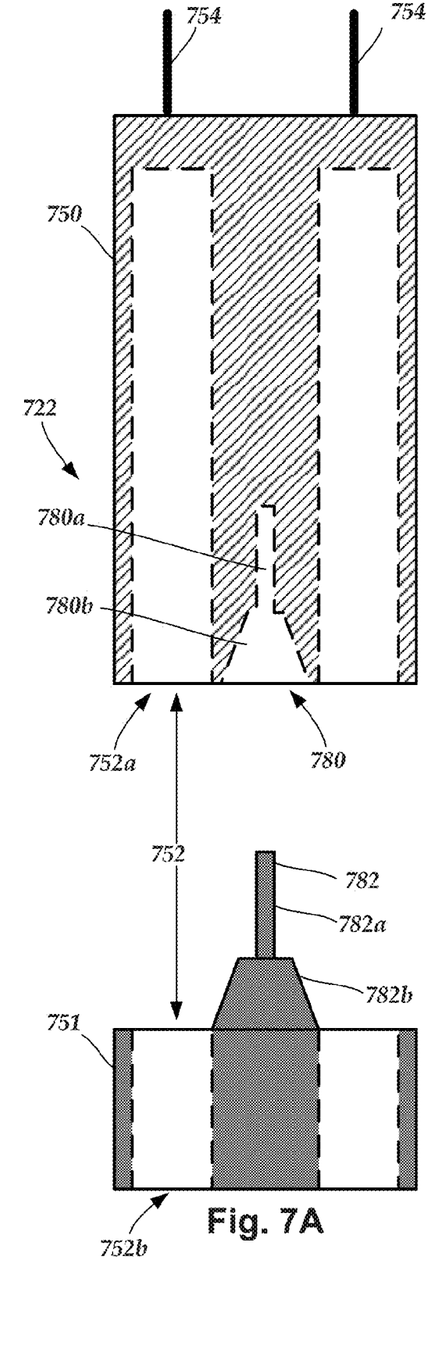
FIG. 7A is a schematic cross-sectional view of a fourth embodiment of a lead extension connector, according to the invention.
Figure 7B:
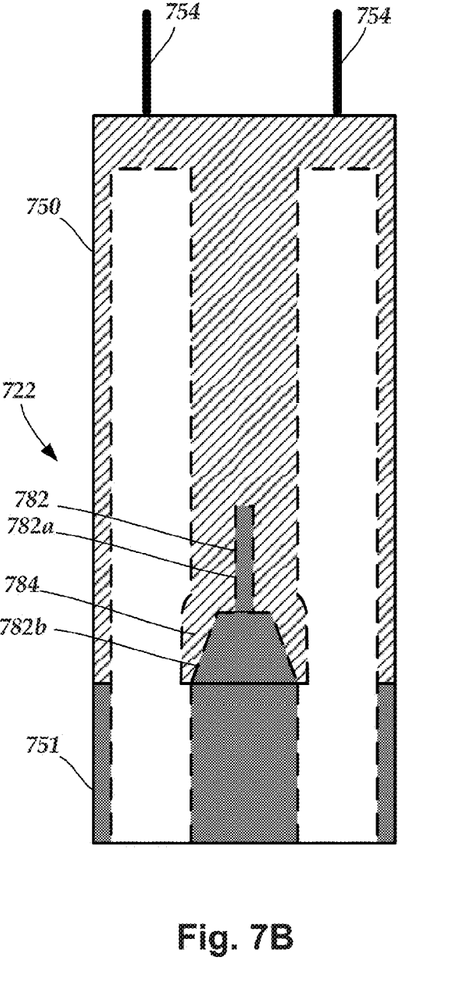
FIG. 7B is a schematic cross-sectional view of the lead extension connector of FIG. 7A with the pin of a second connector body inserted into a pin channel of a first connector body, according to the invention.

FIGS. 7A and 7B illustrate another embodiment of a lead extension connector 722 that is similar to lead extension connector 622 and similarly named elements are the same between the two embodiments unless indicated otherwise. The lead extension connector 722 includes a first connector body 750, a second connector body 751, one or more lead channels 752, and multiple connector contacts (not shown). One or more lead extension bodies 754 extend from the lead extension connector 722. The first connector body 750 has a first portion 752a of each lead channel and further defines a pin channel 780. The second connector body has a second portion 752b of each lead channel and a pin 782.

In this embodiment, the pin 782 has a first portion 782a and a wider second portion 782b. The second portion 782b optionally has sloping sides, as illustrated in FIG. 7A, which slope outwards from the first portion 782a to the main body of the second connector body 751. The pin channel 780 has a corresponding first portions 780a and a wider second portion 780b. In at least some embodiments, the first portion 782a of the pin 782 and the first portion 780a of the pin channel 780 have a same lateral width or diameter. The second portion 782b of the pin 782 is larger in lateral width or diameter than the second portion 780b of the pin channel 780. When the pin 782 is inserted into the pin channel 780, portions 784 of the first connector body 750 adjacent the pin channel 780 are compressed and, consequently, compress adjacent portions of the lead channel 752, as illustrated in FIG. 7B. To release the lead, the second connector body 751 can be pulled back so that the pin 782 exits the pin channel 780 to release the compression and allows the lead to be removed.

Figure 8:
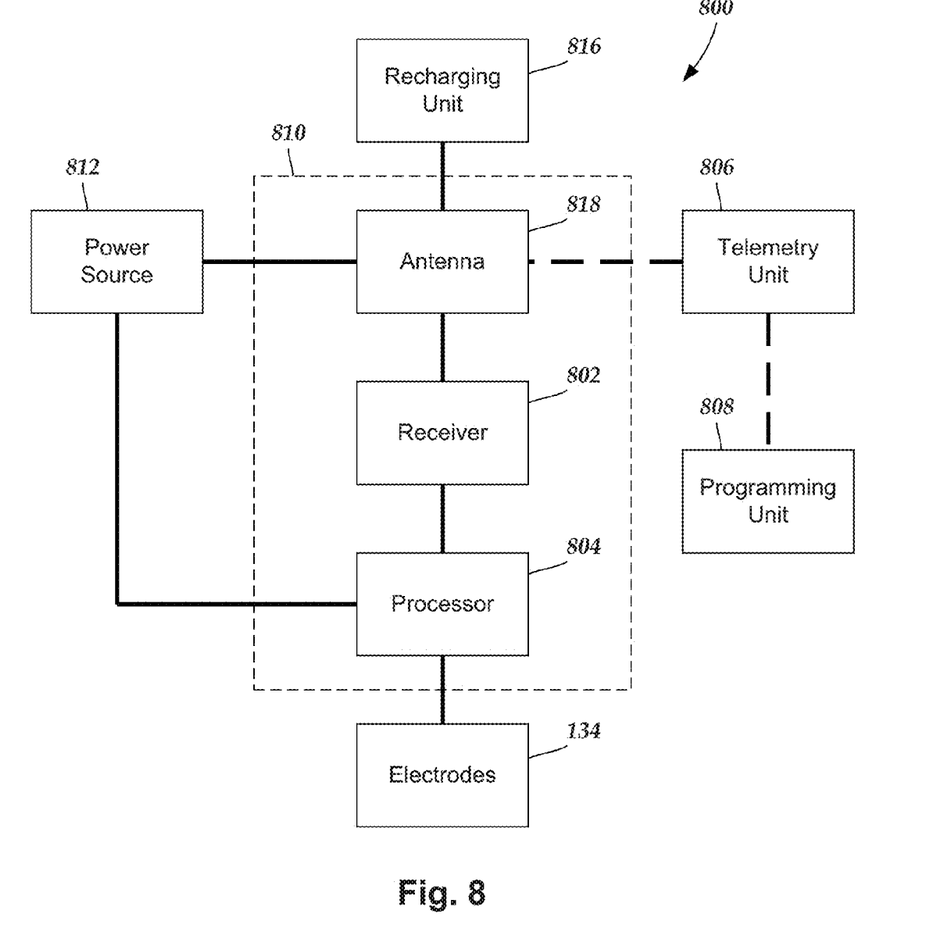
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A lead extension for electrically coupling to at least one implantable electrical stimulation lead, the lead extension comprising:
    at least one lead extension body having a first end portion and an opposing second end portion;
    a plurality of terminals disposed along the first end portion of the at least one lead extension body;
    a lead extension connector disposed along the second end portion of the at least one lead extension body, the lead extension connector configured and arranged to mechanically receive a proximal end portion of at least one electrical stimulation lead, the lead extension connector comprising
        a first connector body defining a pin channel,
        a second connector body comprising a pin, wherein a dimension of the pin is greater than a corresponding dimension of the pin channel,
        at least one lead channel defined within the first and second connector bodies and configured and arranged to receive the at least one electrical stimulation lead, and
        a plurality of connector contacts disposed within the first connector body and configured and arranged to make electrical contact with terminals disposed on the at least one electrical stimulation lead when the at least one electrical stimulation lead is received in the at least one lead channel,
        wherein the pin channel is configured and arranged to receive the pin and, when the pin is received in the pin channel, compress a portion of the first connector body against the at least one electrical stimulation lead in the at least one lead channel to facilitate retention of the at least one electrical stimulation lead within the at least one lead channel; and
    a plurality of conductors extending along the at least one lead extension body and electrically coupling the connector contacts in the lead extension connector to the terminals.

2. The lead extension of claim 1, wherein the at least one lead channel is two lead channels, wherein each lead channel is configured and arranged to receive an electrical stimulation lead.

3. The lead extension of claim 1, wherein the pin comprises a first pin portion and a second pin portion attached to the first pin portion and having sloping sides, wherein the pin channel comprises a first channel portion and a second channel portion adjacent the first channel portion, wherein a dimension of the second pin portion is greater than a corresponding dimension of the second channel portion.

4. An electrical stimulation system, comprising:
the lead extension of claim 1; and
at least one electrical stimulation lead, each electrical stimulation lead having a distal end portion and a proximal end portion and comprising
a plurality of electrodes disposed along the distal end portion of the electrical stimulation lead,
a plurality of terminals disposed along the proximal end portion of the electrical stimulation lead, and
a plurality of conductors electrically coupling the plurality of electrodes to the plurality of terminals,
wherein the proximal end portion of the electrical stimulation lead is insertable into the first and second connector bodies of the lead extension.

5. The electrical stimulation system of claim 4, further comprising a control module configured and arranged to receive the first end portion of the at least one lead extension body and electrically couple to the terminals of the lead extension.

6. A method of coupling an electrical stimulation lead to the lead extension of claim 1, the method comprising:
inserting an electrical stimulation lead in a one of the at least one lead channel defined through both the first and second connector bodies with the first and second connector bodies separated; and
advancing the pin of the second connector body into the pin channel of the first connector body causing the portion of the first connector body to compress against the electrical stimulation lead in the one of the at least one lead channel to facilitate retention of the electrical stimulation lead within the one of the at least one lead channel.

7. The lead extension of claim 1, wherein the dimension of the pin is a diameter of the pin and the dimension of the pin channel is a diameter of the pin channel.

8. The lead extension of claim 1, wherein the dimension of the pin is a lateral width of the pin and the dimension of the pin channel is a lateral width of the pin channel.

9. The lead extension of claim 1, wherein the pin comprises a first pin portion and a second pin portion attached to the first pin portion, wherein the pin channel comprises a first channel portion and a second channel portion adjacent the first channel portion, wherein a dimension of the second pin portion is greater than a corresponding dimension of the second channel portion.

10. The lead extension of claim 9, wherein a dimension of the first pin portion is equal to a dimension of the first channel portion.

11. The lead extension of claim 9, wherein the dimension of the second pin portion is a diameter of the second pin portion and the dimension of the second channel portion is a diameter of the second channel portion.

12. The lead extension of claim 9, wherein the dimension of the second pin portion is a lateral width of the second pin portion and the dimension of the second channel portion is a lateral width of the second channel portion.

13. The lead extension of claim 2, wherein the pin channel is disposed between the two lead channels.

14. The lead extension of claim 1, wherein the first connector body comprises a rigid section and a soft polymeric material covering the rigid section.

15. The lead extension of claim 1, wherein lead extension connector comprises one or more windows through which an observer can determine if the at least one electrical stimulation lead is inserted correctly.

16. The lead extension of claim 3, wherein the dimension of the second pin portion is a diameter of the second pin portion and the dimension of the second channel portion is a diameter of the second channel portion.

17. The lead extension of claim 3, wherein the dimension of the second pin portion is a lateral width of the second pin portion and the dimension of the second channel portion is a lateral width of the second channel portion.

18. The lead extension of claim 3, wherein a dimension of the first pin portion is equal to a dimension of the first channel portion.

19. The method of claim 6, further comprising pulling back the second connector body so that the pin exits the pin channel to release the compression and allow the at least one electrical stimulation lead to be removed.

20. A method of coupling an electrical stimulation lead to the lead extension of claim 2, the method comprising:
inserting a first electrical stimulation lead in a first one of the two lead channels defined through both the first and second connector bodies with the first and second connector bodies separated;
inserting a second electrical stimulation lead in a second of the two lead channels defined through both the first and second connector bodies with the first and second connector bodies separated; and
advancing the pin of the second connector body into the pin channel of the first connector body causing the portion of the first connector body to compress against the first and second electrical stimulation leads in the two lead channels to facilitate retention of the first and second electrical stimulation leads within the two lead channels.

* * * * *